US00PP33030P2

(12) United States Plant Patent
van Langen

(10) Patent No.: US PP33,030 P2
(45) Date of Patent: May 4, 2021

(54) ***ECHEVERIA* PLANT NAMED 'AMIECH2001'**

(50) Latin Name: ***Echeveria elegans* x *Echeveria shaviana***
Varietal Denomination: AMIECH2001

(71) Applicant: NovoAmi B. V., Heerhugowaard (NL)

(72) Inventor: Gerard van Langen, Heerhugowaard (NL)

(73) Assignee: NovoAmi B. V., Heerhugowaard (NL)

( * ) Notice: Subject to any disclaimer, the term of this patent is extended or adjusted under 35 U.S.C. 154(b) by 0 days.

(21) Appl. No.: 16/895,272

(22) Filed: Jun. 8, 2020

(51) Int. Cl.
*A01H 6/32* (2018.01)
*A01H 5/00* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Samuel R. McCoy, Jr.

(57) ABSTRACT

A new and distinct *Echeveria* hybrid plant named 'AMIECH2001' which is characterized by an abundance of foliage held upright in a basal rosette, foliage with lightly serrulate and moderately undulate margins, light greyed-green foliage that is margined nearly white and lightly suffused with blue-green, and the stability of these characteristics from generation to generation.

4 Drawing Sheets

Latin name of the genus and species: The Latin name of the genus and species of the novel variety disclosed herein is *Echeveria elegans* x *Echeveria shaviana.*

Variety denomination: The inventive variety of *Echeveria* hybrid disclosed herein has been given the variety denomination 'AMIECH2001'.

BACKGROUND OF THE INVENTION

Parentage: 'AMIECH2001' is an interspecific hybrid seedling selection resulting from the controlled pollination of an unnamed *Echeveria elegans* plant (not patented), the seed parent, with an unnamed *Echeveria shaviana* plant (not patented), the pollen parent. The crossing was made by the inventor in the spring of 2013 at a commercial greenhouse in Heerhugowaard, the Netherlands. In summer of 2014, one seedling was observed which exhibited unique growth and foliage characteristics. The seedling was isolated for further evaluation in order to confirm the distinctness and stability of the characteristics first observed. In the winter of 2014, upon confirmation of distinctness and stability, 'AMIECH2001' was selected for commercialization.

Asexual Reproduction: Asexual reproduction of the new cultivar 'AMIECH2001', by way of rooting leaf cuttings, was first initiated in the autumn of 2015 at the inventor's commercial greenhouse in Heerhugowaard, the Netherlands. Through five subsequent generations, the unique features of this cultivar have proven to be stable and true to type.

SUMMARY OF THE INVENTION

The cultivar 'AMIECH2001' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH2001'. These characteristics in combination distinguish 'AMIECH2001' as a new and distinct *Echeveria* hybrid cultivar:

1. 'AMIECH2001' exhibits an abundance of relatively small foliage which is tightly held upright in a basal rosette; and
2. 'AMIECH2001' exhibits spatulate foliage that is curved downward at the apex; and
3. 'AMIECH2001' exhibits foliar margins which are lightly serrulate and moderately undulate in juvenile leaves and nearer to entire and less undulated as foliage matures; and
4. 'AMIECH2001' exhibits moderately to strongly glaucous foliage which is light greyed-green and lightly suffused with blue-green, with nearly white margins.

BOTANICAL DESCRIPTION OF THE PLANT

Figure 1:
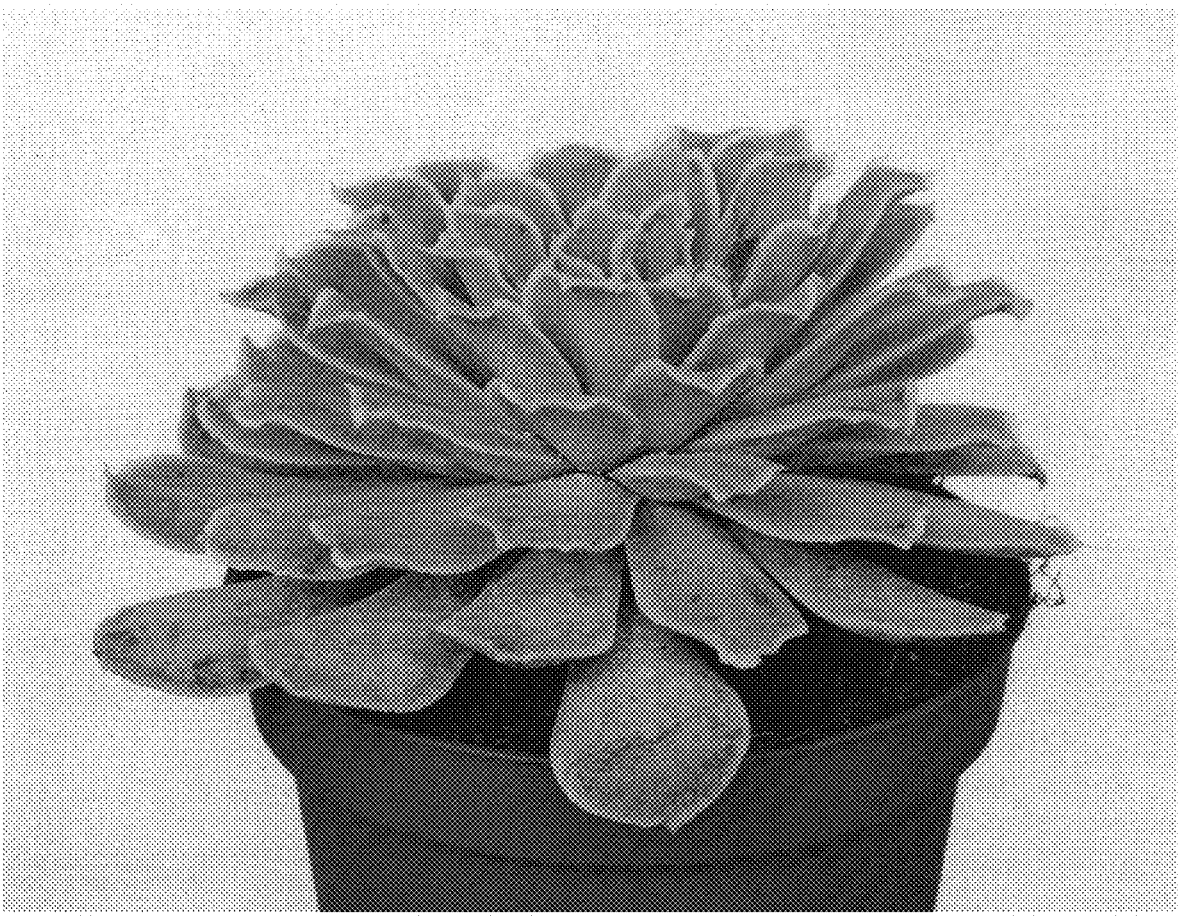
FIG. 1 illustrates, as nearly true as it is reasonably possible to make the same in color photographs of this type, an exemplary plant of 'AMIECH2001' grown in a commercial greenhouse in Heerhugowaard, the Netherlands. This plant is approximately 9 months old, shown planted in an 11 cm container.
Figure 2:
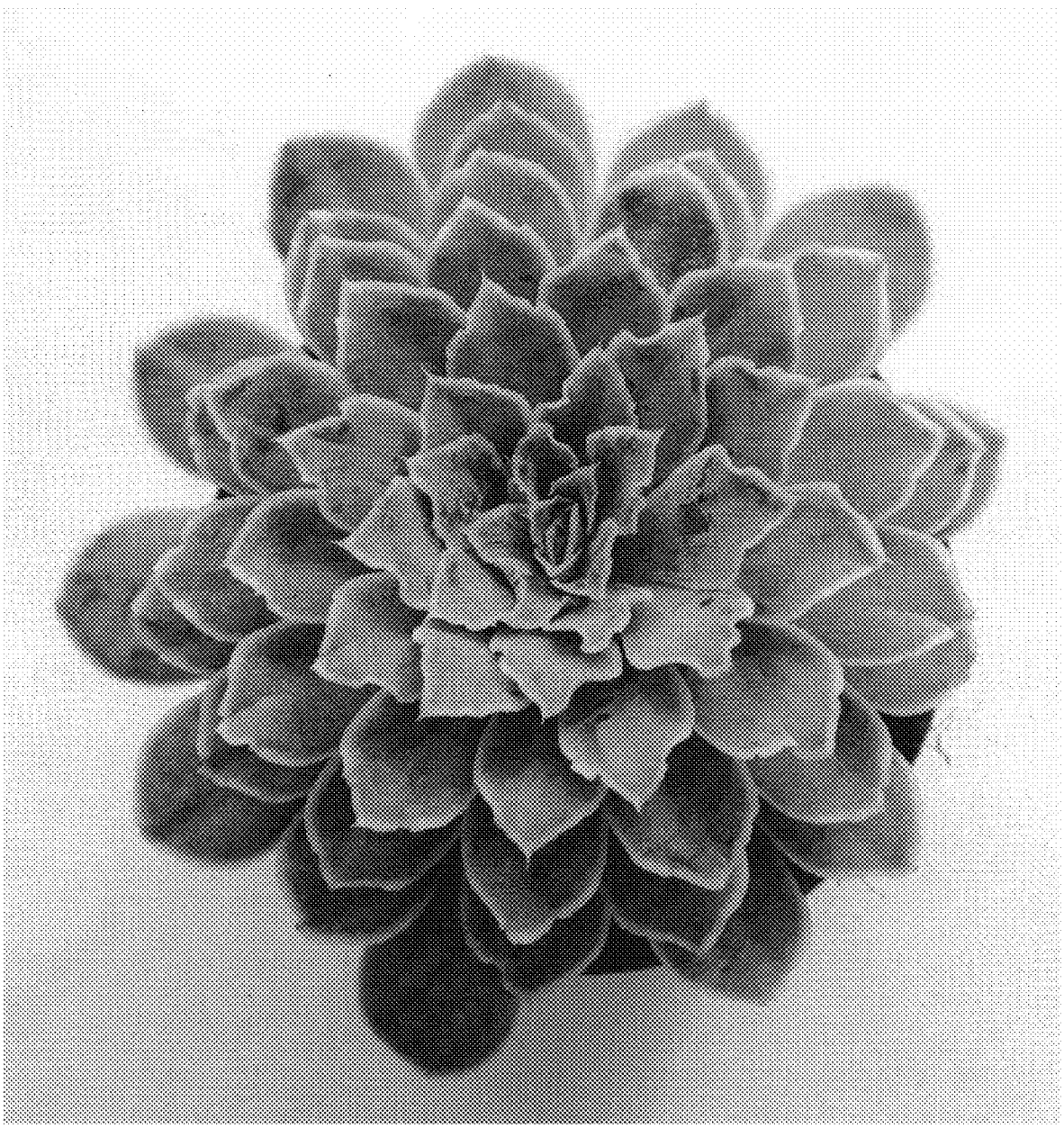
FIG. 2 illustrates, as nearly true as it is reasonably possible to make the same in color photographs of this type, the typical foliage arrangement of 'AMIECH2001.
Figure 3:
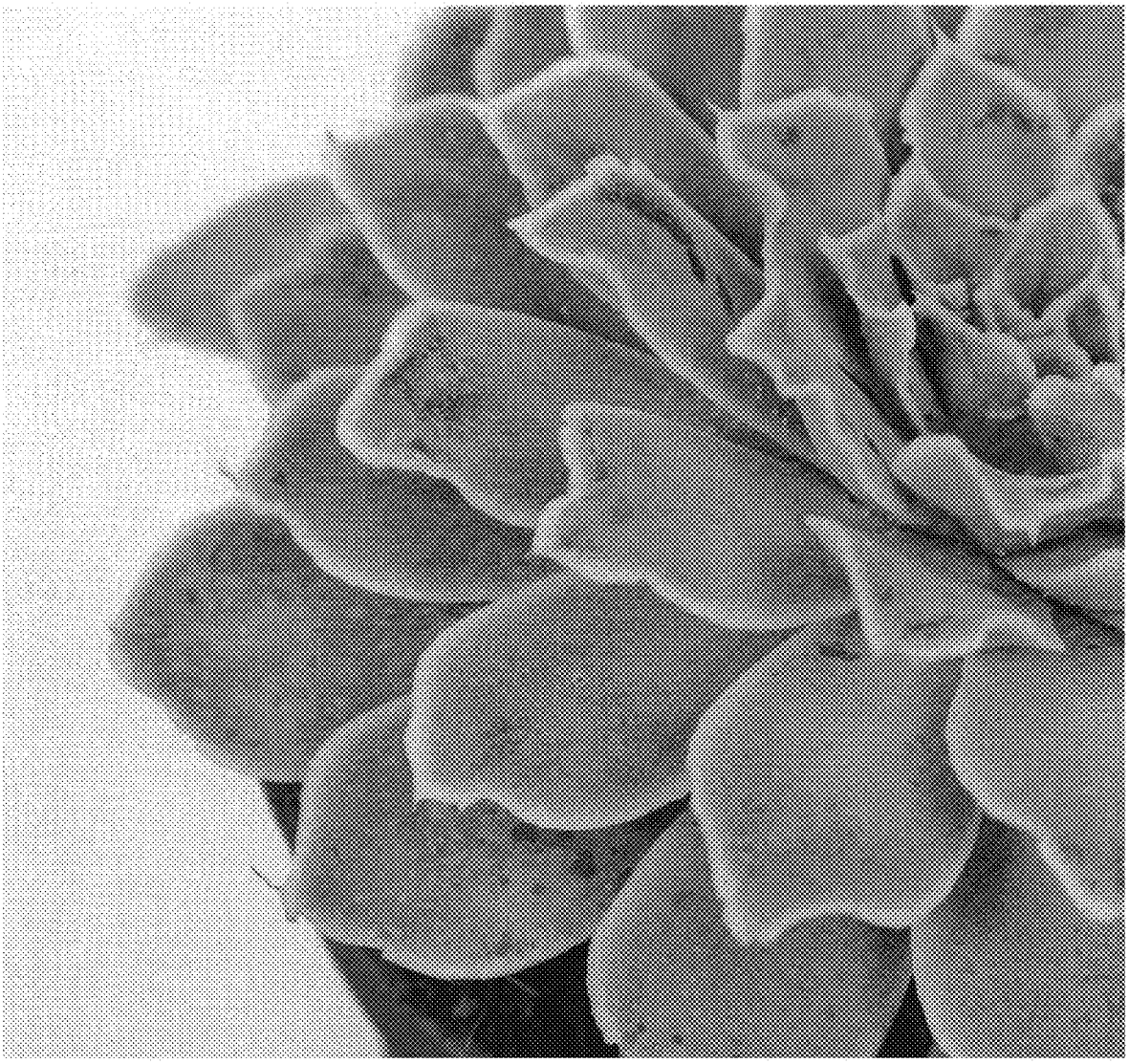
FIG. 3 illustrates, as nearly true as it is reasonably possible to make the same in color photographs of this type, the adaxial surface of the mature foliage 'AMIECH2001'.
Figure 4:
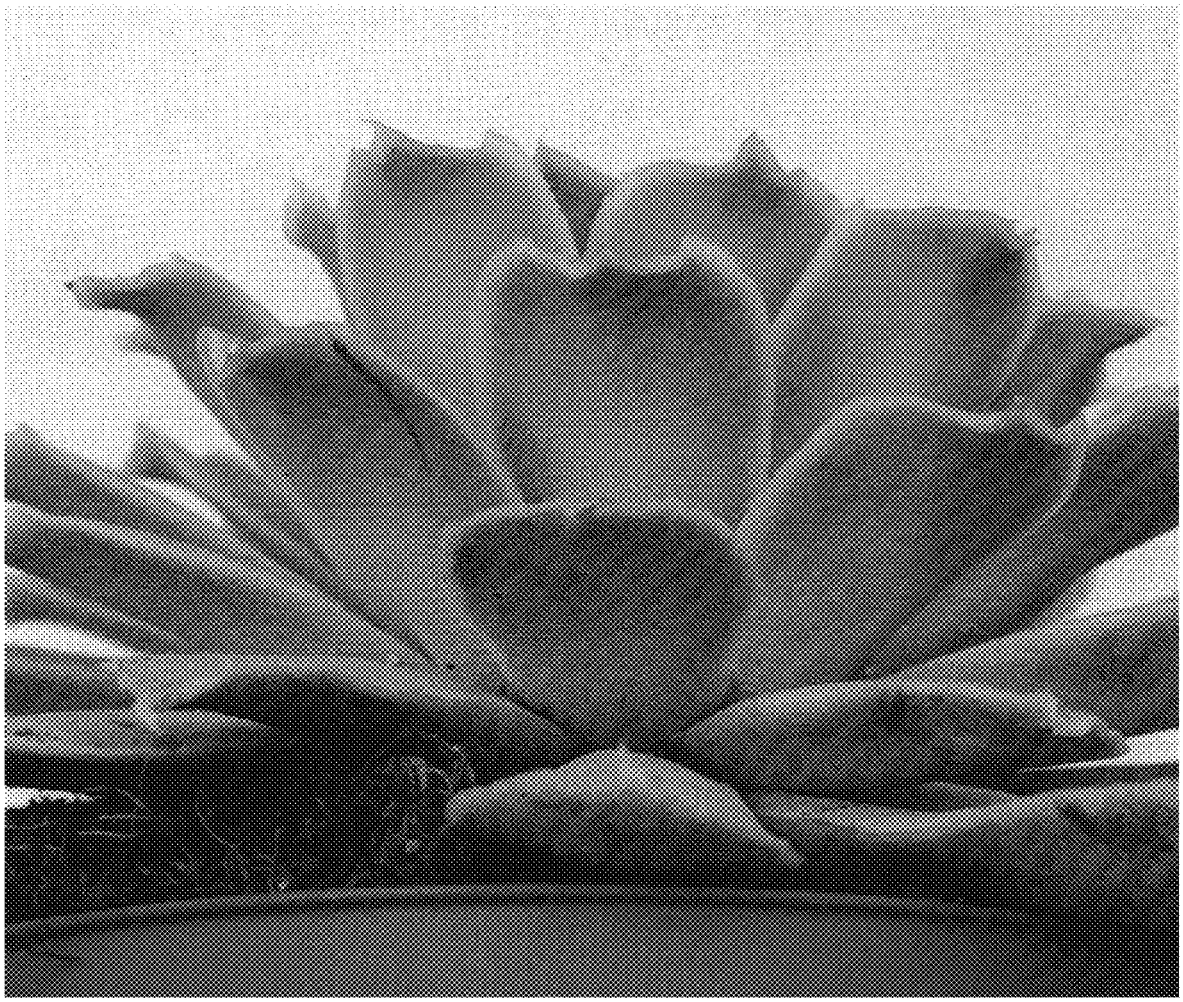
FIG. 4 illustrates, as nearly true as it is reasonably possible to make the same in color photographs of this type, the abaxial surface of the mature foliage 'AMIECH2001'.

The following observations and measurements made in January of 2020 describe averages from a sample set of six specimens of 8 months old 'AMIECH2001' plants grown in 11 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH2001' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, 2015 (sixth edition).

A botanical description of 'AMIECH2001' and comparisons with the parent plants and closest known comparator are provided below.

Plant description:

*Growth habit.*—Succulent perennial with foliage growing in a non-branched basal rosette.

*Plant shape.*—Flattened to flattened globular.

*Height from soil level to top of foliar plane.*—6.0 cm.

*Plant spread.*—Average of 14.5 cm.

*Growth rate.*—Moderately fast growing.

*Plant vigor.*—Moderately vigorous to highly vigorous.

*Propagation.*—Type — Leaf cuttings. Time to initiate rooting — Approximately 21 days at 18 degrees Celsius. Crop time — Approximately 35 weeks to produce a marketable plant in a 7 cm container.

*Disease and pest resistance or susceptibility.*—Neither resistance nor susceptibility to typical *Echeveria* pests and diseases has been observed.

*Environmental tolerances.*—Adapt to, at least, USDA Zones 10 to 12 and temperatures as high as 40 degrees Celsius; moderate tolerance to rain yet drought tolerant once established; high tolerance to wind.

Root system:

*General.*—Fine, well-branched fibrous roots.

Stems:

*Branching habit.*—Leaves in a non-branching basal rosettes; no main branches or lateral branches present.

Foliage:

*Arrangement.*—Rosette.

*Division.*—Simple.

*Attachment.*—Sessile.

*Quantity.*—Approximately 90 leaves per rosette.

*Shape.*—Spatulate.

*Dimensions.*—6.2 cm long, 2.5 cm wide, and 0.6 cm thick, on average.

*Aspect.*—Flat and curved downward at the apex.

*Attitude.*—Juvenile foliage at the center of the rosette is held upward; foliage becomes progressively more relaxed towards the outer whorls of mature foliage, at an average angle of 45 degrees from horizontal.

*Apex.*—Broad acute to apiculate.

*Base.*—Cuneate.

*Margin.*—Juvenile leaves are lightly serrulate and moderately undulate; margins becoming nearer to entire and less undulated as foliage matures.

*Pubescence, texture and luster of the adaxial surface.*—Glabrous, smooth, and matte; moderately to strongly glaucous.

*Pubescence, texture and luster of the abaxial surface.*—Glabrous, smooth, and matte; moderately to strongly glaucous.

*Color.*—Juvenile foliage, adaxial surface — Greyed-green, nearest to RHS 191A; margined lighter, nearest to RHS 190D; the epicuticular glaucous wax covering the leaf surface is greyed-green, nearest to RHS 188A. Juvenile foliage, abaxial surface — Greyed-green, nearest to RHS 191A; margined lighter, nearest to RHS 190D; the epicuticular glaucous wax covering the leaf surface is nearest to in between blue-green and greyed-green, nearest to RHS 122B, 188A and 188B. Mature foliage, adaxial surface — Nearest to in between yellow-green and greyed-green, RHS 147A and 191A, and fading to yellow-green towards the base, nearest to a mixture of RHS 145A and 145B; margined white, nearest to RHS N155A; the epicuticular glaucous wax covering the leaf surface is greyed-green, nearest to RHS 188A. Mature foliage, abaxial surface — Greyed-green, nearest to RHS 191A, and fading to yellow-green towards the base, nearest to a mixture of RHS 145A and 145B; margined white, nearest to RHS N155A; the epicuticular glaucous wax covering the leaf surface is nearest to in between blue-green and greyed-green, nearest to RHS 122B, 188A and 188B. Venation — No venation is visible.

*Petiole.*—No petiole; leaves are sessile.

Inflorescence: No flowering has been observed to date.

Comparisons with the parent plant and closest known comparator: Plants of the new cultivar 'AMIECH2001' differ from the seed parent, an unnamed *Echeveria elegans* plant (not patented), in the following characteristics described in Table 1 below.

TABLE 1

| Characteristic | 'AMIECH2001' | The seed parent. |
|---|---|---|
| Plant size. | Larger than the parent. | Smaller than 'AMIECH2001'. |
| Foliage aspect. | Distal portion of the foliage towards the apex is curved upward. | Flat; not curved upward. |

Plants of the new cultivar 'AMIECH2001' differ from the pollen parent, an unnamed *Echeveria shaviana* plant (not patented), in the following characteristics described in Table 2 below.

TABLE 2

| Characteristic | 'AMIECH2001' | The pollen parent. |
|---|---|---|
| Plant size. | Smaller than the parent. | Larger than 'AMIECH2001'. |
| Foliage margins. | Juvenile leaves are lightly serrulate and moderately undulate; margins nearer | Juvenile leaves are lightly serrulate and lightly undulate; margins nearer |

TABLE 2-continued

| Characteristic | 'AMIECH2001' | The pollen parent. |
|---|---|---|
| | to entire and less undulated as foliage matures. | to entire and not undulated as foliage matures. |
| General coloration of the foliage. | Light greyed-green and lightly suffused blue-green. | Generally appearing as purple suffused with pink. |

Comparisons with the closest known comparator: Plants of the new cultivar 'AMIECH2001' differ from the closest known commercial comparator, *Echeveria* hybrid 'Canadian' (not patented), in the following characteristics described in Table 3 below.

TABLE 3

| Characteristic | 'AMIECH2001' | 'Canadian' |
|---|---|---|
| Foliage size. | Smaller than 'Canadian'. | Larger than 'AMIECH2001'. |
| Foliage attitude. | More upright than 'Canadian'. | More relaxed than 'AMIECH2001'. |
| Foliage aspect. | Curved downward at the apex. | Flat; not curved at the apex. |

That which is claimed is:

1. A new and distinct variety of *Echeveria* hybrid plant named 'AMIECH2001', substantially as described and illustrated herein.

* * * * *